Figure 1:
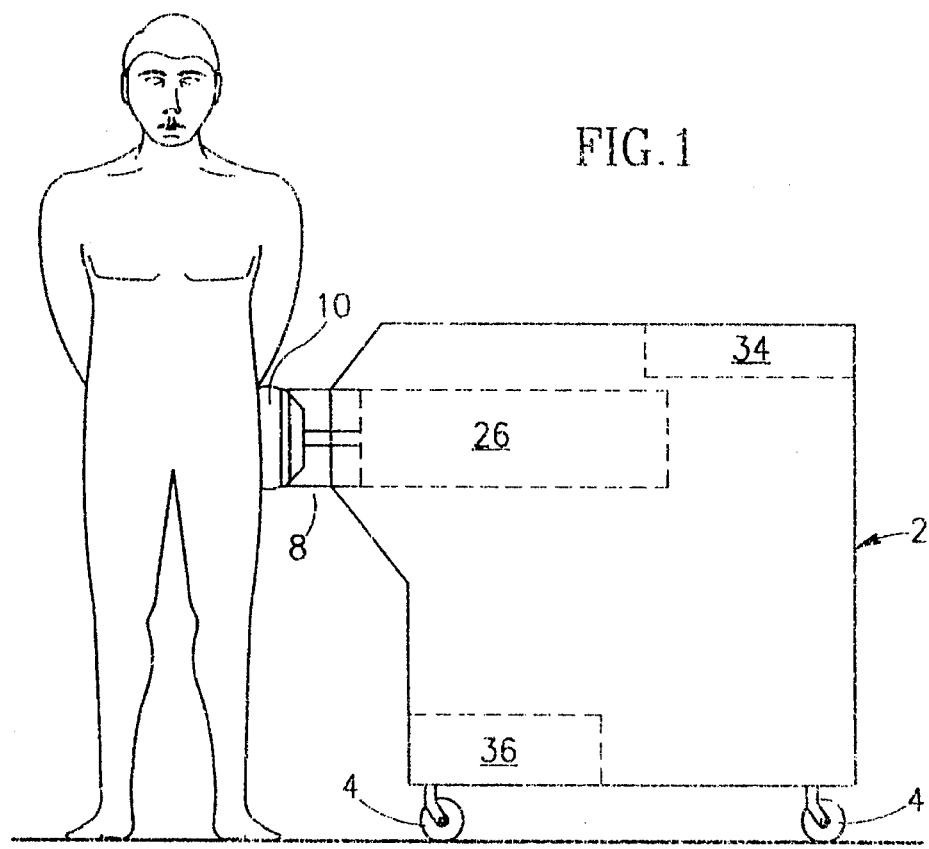

United States Patent [19]

Spector

[11] Patent Number: 5,529,572
[45] Date of Patent: Jun. 25, 1996

[54] METHOD AND APPARATUS PARTICULARLY USEFUL FOR TREATING OSTEOPOROSIS

[75] Inventor: Avner Spector, Savyon, Israel

[73] Assignee: Medispec Ltd., Rockville, Md.

[21] Appl. No.: 256,542

[22] PCT Filed: Jan. 21, 1993

[86] PCT No.: PCT/US93/00338

§ 371 Date: Jul. 13, 1994

§ 102(e) Date: Jul. 13, 1994

[87] PCT Pub. No.: WO93/14720

PCT Pub. Date: Aug. 5, 1993

[30] Foreign Application Priority Data

Jan. 24, 1992 [IL] Israel ......................... 100750

[51] Int. Cl.⁶ ..................................... A61N 7/00

[52] U.S. Cl. ............................. 601/2; 367/147; 367/175

[58] Field of Search ....................... 601/2–4; 128/660.03; 607/50, 51; 367/141, 142, 147, 175; 181/142

[56] References Cited

U.S. PATENT DOCUMENTS

| 4,890,603 | 1/1990 | Filler .......................................... 601/4 |
| 4,905,671 | 3/1990 | Senge et al. ................................ 601/2 |
| 4,905,672 | 3/1990 | Schwarze et al. ........................... 601/2 |
| 4,979,501 | 12/1990 | Valchanov et al. .......................... 601/2 |

*Primary Examiner*—Ruth S. Smith
*Attorney, Agent, or Firm*—Mark M. Friedman

[57] ABSTRACT

A method and apparatus for increasing the density and strength of bone, particularly for preventing or treating osteoporosis, by subjecting the bone to unfocussed compressional shock waves.

15 Claims, 2 Drawing Sheets

METHOD AND APPARATUS PARTICULARLY USEFUL FOR TREATING OSTEOPOROSIS

The present invention relates to a method and apparatus particularly useful for treating osteoporosis.

Osteoporosis is a bone disorder which affects middle and old age people, especially women. It is characterized by an abnormal loss of bone tissue, and consequently by a decrease in the density of the bone. The reduction in bone density reduces the strength of the bone such as to make the afflicted person susceptible to easy fracture, particularly of the pelvis (hip), spine, femoral neck, and forearm.

Osteoporosis affects millions of elderly people. In the USA, it affects about one out of every four women over the age of 45, and half of all women over the age of 60. Each year approximately 200,000 persons break a hip because of osteoporosis. It is therefore one of the major causes for prolonged hospitalization of the elderly; and resulting complications, particularly from hip fracture, constitute a frequent cause of death in the USA.

At the present time there is no generally accepted cure for osteoporosis, although various treatments are used with varying degrees of success. Thus, calcium supplementation, regular exercise, and enhanced physical activity may prevent deterioration of the bone; and at a later stage, more elaborate treatment, such as the administering of hormones, calcium, phosphate and vitamin D analogues may be used.

An object of the present invention is to provide a novel method of increasing the density and strength of the bone, particularly for preventing or treating osteoporosis. Another object of the invention is to provide apparatus for use in such treatment.

According to one aspect of the present invention, there is provided a method of increasing the density and strength of the bone, particularly for preventing or treating osteoporosis comprising subjecting the bone to unfocussed compressional shock waves. Such unfocussed shock waves thus produce dynamic repetitive loading of the bone. This increases the mean bone density, and thereby strengthens the bone against fracture.

According to further features in the preferred embodiments of the invention described below, the unfocussed shock waves are applied to the bone at an intensity of 50–500 atmospheres, and in the form of substantially planar, unfocussed wavefronts covering an area of from 10 to 150 cm$^2$ of the bone.

According to one described embodiment, the unfocussed shock waves are applied by a point-source shock wave generator located at the focal point of a paraboloidal reflector which reflects the shock waves to form a substantially planar, unfocussed wavefront. More particularly, in the described preferred embodiment the shock waves are generated by a spark gap, preferably an electrical spark gap.

A second embodiment is described wherein the shock waves are generated by an area-source shock wave generator, particularly an electromagnetic device.

Generally speaking, the shock waves may be generated by the same types of shock wave generators as are used in lithotripters, namely devices designed to fragment upper urinary tract stones, gallstones, etc., by focussing shock waves on the stones. The shock waves may be of substantially the same duration and rate as in lithotripters, except that instead of applying shock waves in a focussed condition, in the present invention the shock waves are applied in an unfocussed condition so as to repetitively and dynamically load a substantial area of the bone being treated.

The invention also provides apparatus for increasing the density and strength of the bone, particularly for preventing or treating osteoporosis, in accordance with the above method.

Further features and advantages of the invention will be apparent from the description below.

Figure 2:
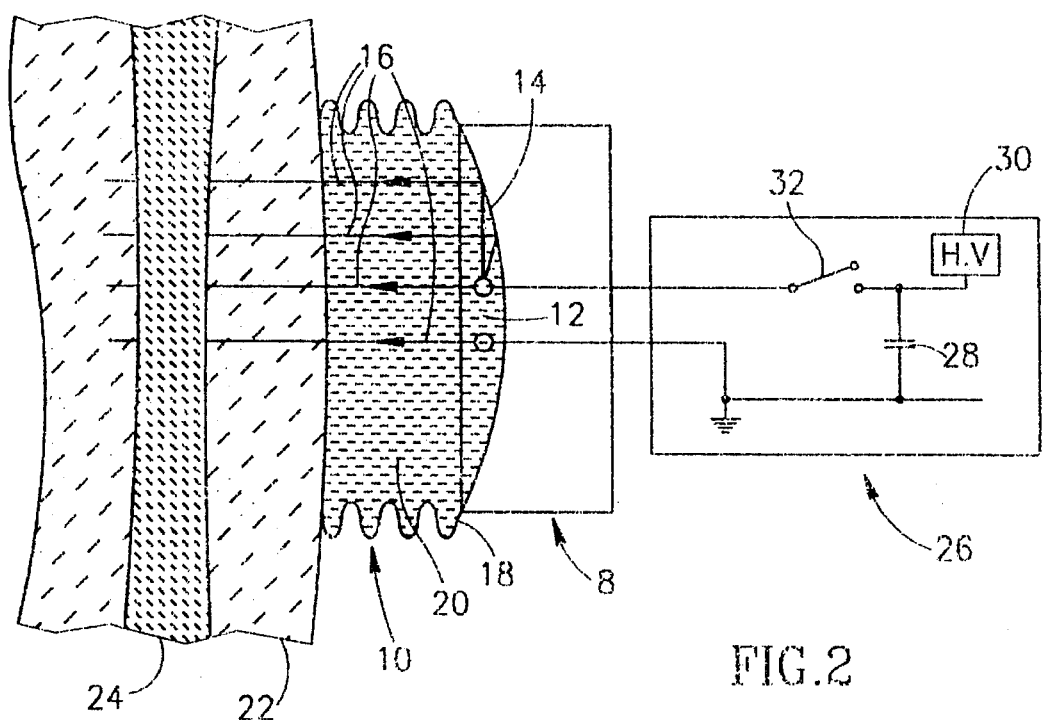
Figure 3:
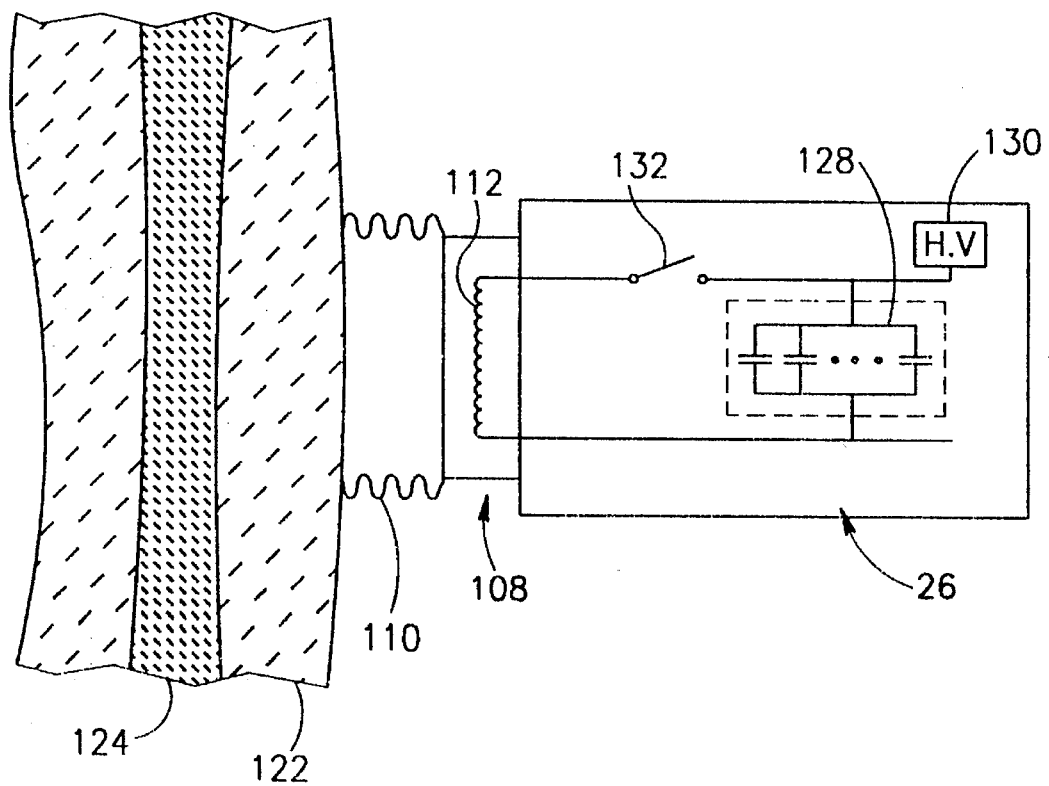

The invention is herein described, by way of example only, with reference to the accompanying drawings, wherein:

FIG. 1 diagrammatically illustrates one form of apparatus constructed in accordance with the present invention;

FIG. 2 is an enlarged view of the main parts of the apparatus of FIG. 1 involved in the treatment of bone in accordance with the present invention; and FIG. 3 is a view similar to that of FIG. 2 but illustrating a variations in the apparatus.

The apparatus illustrated in FIG. 1, and therein designated 2, may basically be a known lithotripter apparatus used for fragmenting stones, e.g., kidney stones, except that the shock waves produced are in an unfocussed condition rather than in a focussed condition as in a lithotripter. In addition, the apparatus 2 is preferably mounted on wheels 4 to make it mobile and thereby to facilitate its application to any desired bone of a patient 6, such as the pelvis or femur exhibiting osteoporosis. The treatment is effected by a shock wave generator, generally designated 8, projecting from one side of the apparatus 2 and adapted to be coupled to the bone being treated by an acoustical coupling 10. The unfocussed shock waves are applied via the acoustic coupler 10 as substantially planar, unfocussed wavefronts covering a relatively large area of the bone being treated, e.g., an area of from 10 to 150 cm$^2$.

The manner of generating and applying the unfocussed shock waves is more particularly illustrated in FIG. 2. Thus, the unfocussed shock wave generator 8 is shown as including a spark gap 12 at the focal point of a paraboloidal reflector 14. Such a reflector, when the shock wave generator is located at its focal point, reflects the shock waves in a "collimated" (unfocussed) form to produce a substantial planar, unfocussed wavefront. Reflector 14 thus reflects the shock waves to form a substantially planar, unfocussed wavefront, which are propagated through the acoustical coupler 10, as indicated by lines 16.

The construction illustrated in FIG. 2, including a paraboloidal reflector 14 with the spark gap 12 located at its focal point, it is to be clearly distinguishes from a conventional lithotripter producing a focussed shock wave. Thus, the conventional lithotripter uses an ellipsoidal reflector with the shock wave generator located at one focal point thereof, so that the generated shock waves are focussed at the second focal point of the ellipsoidal reflector where the kidney stone, or other object to be fragmented, is located.

The acoustical coupler 10, through which the generated shock waves are coupled to the patient, may also be of the type used in lithotripters. Thus, the acoustic coupler 10 includes a flexible envelope 18 containing a coupling liquid 20, such as water. A suitable acoustic gel may be provided where the envelope contacts the patient to effect good acoustic coupling to the patient.

As shown in FIG. 2, the acoustic coupler 10 directly contacts the flesh 22 of the patient. The patient's flesh has substantially the same density as the water 20 (or other liquid) used in the acoustic coupler 10, so that the generated unfocussed shock wave propagates through it in substantially the same form as through the acoustic coupler 10. The bone 24 of the subject, however, is of a substantially different density from that of either the flesh 22 or the liquid 20 in the acoustic coupler 10, and therefore the unfocussed shock waves apply a compressional force against the bone 24.

It will thus be seen that the repetitve application of the unfocussed shock waves to the patient's skin will subject the bone 24 to dynamic repetitive loads. Such loads increase the mean bone density of the bone 24, and thereby strengthen the treated bone against the possibility of fracture.

In the apparatus illustrated in FIGS. 1 and 2, the shock wave generator 8 is of the spark gap type. It is supplied by a high voltage generator 26 including a capacitor 28 (or bank of capacitors) charged by a high voltage source 30 and periodically discharged by a switch 32 to apply the high voltage to the spark plug 12 in the shock wave generator 8.

The apparatus illustrated in FIG. 1 further includes a control panel, schematically indicated by box 34, and a water system, schematically illustrated by box 36, for supplying water to the acoustic coupler 10.

Instead of using a point-source type shock wave generator for generating the unfocussed shock waves as illustrated in FIGS. 1 and 2, there may also be used an area-source type shock wave generator, such as one that includes an electromagnetic device for generating the shock waves. Examples of such electromagnetic-type shock wave generators are described in U.S. Pat. Nos. 4,674,505, 4,796,608 and 4,782,821. Such an electromagnetic-type shock wave generator is schematically illustrated in FIG. 3.

Thus, as shown in FIG. 3, the shock wave generator, therein designed 108, includes an electromagnetic device 112, such as a flat pancake coil, which is energized by a bank of capacitors 128 charged by a high voltage source 130 and periodically discharged through the electromagnetic device 112 by the closing of an electrical switch 132. The apparatus illustrated in FIG. 3 also includes an acoustical coupler 110 for propagating the generated shock waves in an unfocussed condition via the patient's flesh 122 to the patient's bone 124, in the same manner as described above with respect to FIGS. 1 and 2.

Other types of shock wave generators, as used in lithotripter devices, may also be used in the present method, except of course the generated shock waves are applied in an unfocussed condition to the bone, rather than in a focussed condition. For example, the shock wave generator could also be of the piezoelectric crystal type, as described for example in U.S. Pat. No. 4,617,931. Generally speaking, except for the fact that the shock waves are applied in an unfocussed condition, rather than in a focussed condition as in the conventional lithotripters, the shock waves may be generated and applied for the same durations and at the same frequencies as in the conventional lithotripters.

The unfocussed shock waves preferably are applied over a relatively large surface of the bone to be treated, for example to cover an area of from 10 to 150 cm$^2$. The intensity of the shock waves may be from 50–500 atmospheres. Each shock wave is of a duration of a few microseconds, as in a conventional lithotripter, and is preferably applied at a frequency of 1–10 shock waves per second, for a period of 5–30 minutes in each treatment. The number of treatments depends on the particular patient. Such a treatment as described above subjects the bone to dynamic repetitive loads, and thereby strengthens the bone by increasing its mean density.

While the invention has been described with respect to two preferred embodiments, it will be appreciated that these are set forth merely for purposes of example, and that many other variations, modifications and applications of the invention may be made.

What is claimed is:

1. A method of increasing the density and strength of bone, comprising subjecting said bone to substantially planar, collimated compressional shock waves having a substantially constant intensity as a function of distance from a shock wave source, and wherein said collimated shock waves are applied to the bone at an intensity of 50–500 atmospheres.

2. The method according to claim 1, wherein said collimated shock waves are applied in the form of a substantially planar, collimated wavefront covering an area of from 10 to 150 cm$^2$ of the treated bone.

3. The method according to claim 1, wherein said collimated shock waves are applied by a point-source shock wave generator located at the focal point of a paraboloidal reflector which reflects the shock waves to form a substantially planar, collimated wavefront.

4. The method according to claim 3, wherein the collimated shock waves are propagated from the reflector to the bone via a liquid compressional-wave acoustic coupler.

5. The method according to claim 3, wherein said shock waves are generated at said focal point of the paraboloidal reflector by a spark gap.

6. The method according to claim 1, wherein said collimated shock waves are generated by an area-source shock wave generator.

7. The method according to claim 1, wherein said collimated shock waves are applied to bone at a rate of 1–10 shock waves per second.

8. The method according to claim 1, wherein said collimated shock waves are applied to the bone for periods of 5–30 minutes each.

9. Apparatus for increasing the density and strength of bone, comprising: a shock wave generator for generating compressional shock waves, including a collimator for applying the generated shock waves in a substantially planar, collimated condition to the bone, said shock waves having a substantially constant intensity as a function of distance from said shock wave generator, and wherein said shock wave generator generates shock waves of an intensity of 50–500 atmospheres.

10. The apparatus according to claim 9, wherein said shock wave generator includes a point-source shock wave generator, and said collimator for applying the generated shock waves in a collimated condition to the bone includes a paraboloidal reflector, said point source shock wave generator being located at the focal point of the paraboloidal reflector.

11. The apparatus according to claim 10, wherein said point-source shock wave generator includes a spark gap.

12. The apparatus according to claim 9, further comprises a liquid compressional-wave acoustic coupler through which the generated shock waves are coupled to the patient.

13. The apparatus according to claim 12, further comprising wheels located under the apparatus thereby providing mobility to enable moving said acoustic coupler against the skin of the patient whose bone is to be treated.

14. The apparatus according to claim 9, wherein said shock wave generator includes an area-source shock wave generator.

15. The apparatus according to claim 14, wherein said area-source shock wave generator includes an electromagnetic device.

* * * * *